United States Patent
Orr et al.

(10) Patent No.: US 10,869,614 B2
(45) Date of Patent: Dec. 22, 2020

(54) SYSTEM FOR PERFORMING HISTOGRAM ANALYSIS OF THE TIME-BASED CAPNOGRAPHY SIGNALS AND METHOD OF OPERATION THEREOF

(71) Applicant: KONINKLIJKE PHILIPS N.V., Eindhoven (NL)

(72) Inventors: Joseph Allen Orr, Park City, UT (US); Lara Marie Brewer, Bountiful, UT (US)

(73) Assignee: Koninklijke Philips N.V., Eindhoven (NL)

( * ) Notice: Subject to any disclaimer, the term of this patent is extended or adjusted under 35 U.S.C. 154(b) by 685 days.

(21) Appl. No.: 15/540,151

(22) PCT Filed: Dec. 16, 2015

(86) PCT No.: PCT/IB2015/059652
§ 371 (c)(1),
(2) Date: Jun. 27, 2017

(87) PCT Pub. No.: WO2016/108121
PCT Pub. Date: Jul. 7, 2016

(65) Prior Publication Data
US 2017/0367620 A1 Dec. 28, 2017

Related U.S. Application Data

(60) Provisional application No. 62/098,367, filed on Dec. 31, 2014.

(51) Int. Cl.
*A61B 5/083* (2006.01)
*G06F 3/01* (2006.01)
*A61B 5/00* (2006.01)

(52) U.S. Cl.
CPC .......... *A61B 5/0836* (2013.01); *A61B 5/7221* (2013.01); *G06F 3/01* (2013.01)

(58) Field of Classification Search
CPC ....... A61B 5/0836; A61B 5/7221; A61B 3/01; A61B 5/08; A61B 5/0816; A61B 5/082; A61B 5/0833

(Continued)

(56) References Cited

U.S. PATENT DOCUMENTS 6,033,368 A * 3/2000 Gaston, IV ............ A61B 5/083 422/84
6,419,634 B1 * 7/2002 Gaston, IV ............ A61B 5/083 422/84

(Continued)

FOREIGN PATENT DOCUMENTS

JP 2011206286 A 10/2011

*Primary Examiner* — Navin Natnithithadha
(74) *Attorney, Agent, or Firm* — Daniel H. Brean

(57) ABSTRACT

A gas concentration monitoring system (100, 600) may include a processor (110, 610) configured to detect a concentration of a selected gas in a sample gas flow obtained from a physical interface (107) to a patient (101); form a dataset including a plurality of data points, each data point corresponding to the detected concentration of the selected gas within the sample gas flow during a sampling time; group the data points according to a frequency of occurrence of the data points within the sampling time; and/or determine at least one of a signal confidence and signal quality based on relative characteristics between the groups of data points.

20 Claims, 8 Drawing Sheets

(58) Field of Classification Search
USPC .................................................. 600/529–543
See application file for complete search history.

(56) References Cited

U.S. PATENT DOCUMENTS

| | | | |
|---|---|---|---|
| 6,534,769 B1 * | 3/2003 | Graham | A61B 5/0836 |
| | | | 250/343 |
| 6,866,637 B2 * | 3/2005 | George | A61B 5/0813 |
| | | | 600/532 |
| 7,305,987 B2 | 12/2007 | Scholler et al. | |
| 7,427,269 B2 * | 9/2008 | George | A61B 5/083 |
| | | | 600/529 |
| 7,662,106 B2 | 2/2010 | Daniels et al. | |
| 8,398,555 B2 | 3/2013 | Ochs et al. | |
| 9,763,600 B2 | 9/2017 | Van Kesteren et al. | |
| 10,070,804 B2 * | 9/2018 | Eichler | G01N 33/497 |
| 10,342,939 B2 * | 7/2019 | Armitstead | A61M 16/0057 |
| 2007/0149891 A1 * | 6/2007 | George | A61B 5/0813 |
| | | | 600/533 |
| 2008/0059224 A1 | 3/2008 | Schechter | |
| 2008/0114551 A1 | 5/2008 | Roecker | |
| 2009/0203972 A1 | 8/2009 | De Chazal et al. | |
| 2011/0245705 A1 | 10/2011 | Brewer et al. | |
| 2012/0016218 A1 | 1/2012 | Armitstead et al. | |
| 2012/0310104 A1 | 12/2012 | Van Kesteren et al. | |
| 2013/0245483 A1 * | 9/2013 | Eichler | G01N 33/497 |
| | | | 600/532 |
| 2014/0007878 A1 | 1/2014 | Armitstead et al. | |
| 2014/0288440 A1 | 9/2014 | Asher et al. | |
| 2016/0151590 A1 | 6/2016 | Porcyk | |
| 2016/0256072 A1 * | 9/2016 | Eichler | A61B 5/097 |

* cited by examiner

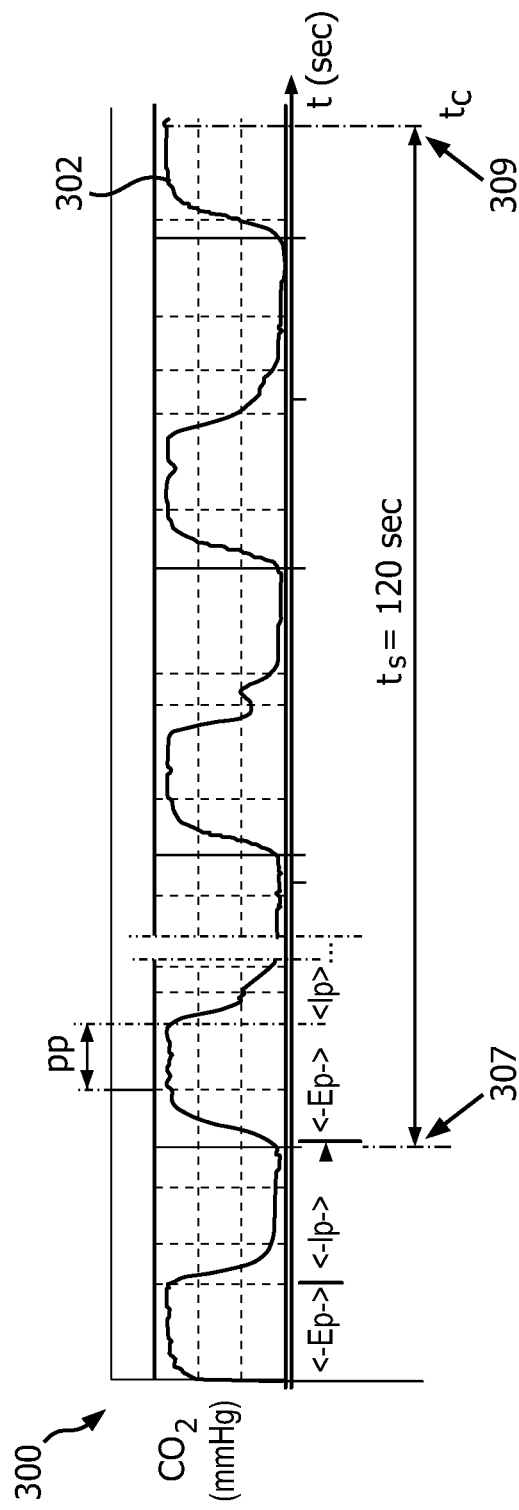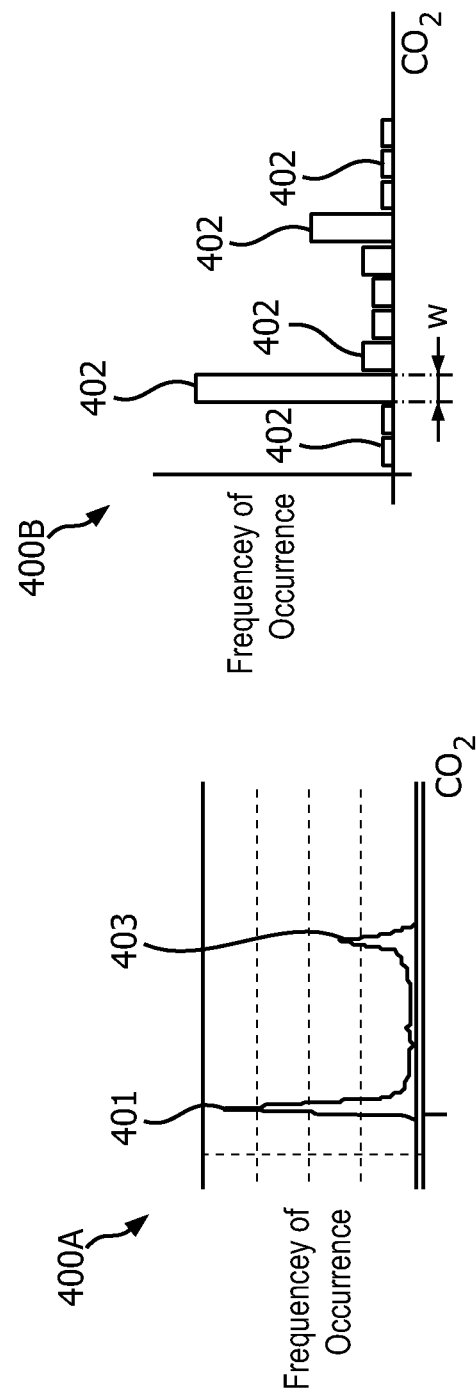

SYSTEM FOR PERFORMING HISTOGRAM ANALYSIS OF THE TIME-BASED CAPNOGRAPHY SIGNALS AND METHOD OF OPERATION THEREOF

This application is a national stage application under 35 U.S.C. § 371 of International Application No. PCT/IB2015/059652 filed on Dec. 16, 2015 and published in the English language on Jul. 7, 2016 as International Publication No. WO 2016/108121, which claims priority to U.S. Application No. 62/098,367 filed on Dec. 31, 2014, the entire disclosures of which are incorporated herein by reference.

The present system relates to monitoring capnography signals, such as for performing histogram analysis of a carbon dioxide ($CO_2$) waveform to identify periods of breath instability without a need to identify individual breaths, and a method of operation thereof.

Typically, capnometry may be used to detect periods of slow and/or inadequate breathing in patients who may be at risk of inadequate ventilation such as those who are administered analgesic and/or sedative medications or otherwise in respiratory distress. Accordingly, it is desirable to monitor the stability of breaths of these patients using a capnogram so that proper medical care can be exercised.

However, conventional algorithms which determine the stability of breaths based on a capnometry waveform require the detection of individual breaths, and comparison of characteristic features of the detected breaths over a time period to enable breathing parameters to be determined. Unfortunately, with conventional methods, if the breath detection algorithm fails, it is likely that the parameters derived from each of the detected breaths are also in error. These conventional algorithms require considerable system resources to properly identify each individual breath in real time. Further, the addition of supplemental oxygen may correspondingly increase the inaccuracy of capnogram readings making in more difficult to determine stability of breaths using conventional methods. Accordingly, embodiments of the present system may overcome these and/or other disadvantages in prior systems.

The system(s), device(s), method(s), arrangements(s), user interface(s), computer program(s), processes, etc. (hereinafter each of which will be referred to as system, unless the context indicates otherwise), described herein address problems in prior art systems.

In accordance with embodiments of the present system, there is disclosed a gas concentration monitoring system which may include a processor which may be configured to detect a concentration of a selected gas in a sample gas flow obtained from a physical interface to a patient from a dataset including a plurality of data points, each data point corresponding to the detected concentration of the selected gas within the sample gas flow during a sampling time; group the data points according to a frequency of occurrence of the data points within the sampling time; and/or determine at least one of a signal confidence and signal quality based on relative characteristics between the groups of data points.

In accordance with embodiments of the present system, the processor may be further configured to group the data points with each grouping corresponding to a different range of concentrations of the selected gas. The processor may be further configured to determine the at least one of a signal confidence and signal quality based upon a relative number of data points that are present within the groups of data points. The gas concentration monitoring system may further include a rendering device coupled to the processor, wherein the processor may be configured to render the groups of data points as a histogram on the rendering device. The processor may be further configured to identify two groups of data points that correspondingly have a largest and next largest number of data points amongst the groups of data points.

In accordance with embodiments of the present system, the processor may be further configured to determine a number of data points between the two groups of data points and is configured to determine the at least one of a signal confidence and signal quality based upon the determined number of data points. In accordance with yet further embodiments of the present system, the sampling time interval may encompass at least a plurality of breath cycles each breath cycle including inspiration and expiration phases or a period of at least 20 seconds, whichever may be determined to occur first. It is also envisioned that the physical interface may include a nasal cannula or mask (108) configured for coupling to the patient. Moreover, the system may further include a pneumatic system controlled by the processor to provide a ventilation gas mixture to the physical interface for inhalation by the patient.

In accordance with embodiments of the present system, there is provided a method of monitoring capnography signals. The method may include acts of detecting a concentration of a selected gas in a sample gas flow obtained from a physical interface to a patient; forming a dataset including a plurality of data points, each data point corresponding to the detected concentration of the selected gas within the sample gas flow during a sampling time; grouping the data points according to a frequency of occurrence of the data points within the sampling time; and/or determining at least one of a signal confidence and signal quality based on relative characteristics between the groups of data points. The act of grouping the data points may further include an act of grouping the data points based on different ranges of concentrations of the selected gas. It is also envisioned that the act of determining the at least one of a signal confidence and signal quality may further include an act of determining a relative number of data points that are present within the groups of data points. The method may further include an act of rendering the groups of data points as a histogram on a rendering device. The method may further include an act of identifying two groups of data points that correspondingly have a largest and next largest number of data points amongst the groups of data points. The method may further include an act of determining a number of data points between the two groups of data points, wherein the act of determining the at least one of a signal confidence and signal quality is based upon the determined number of data points. In accordance with embodiments of the present system, the sampling time interval may encompasses at least a plurality of breath cycles each breath cycle including inspiration and expiration phases or a period of at least 20 seconds, whichever may be determined to occur first.

In accordance with embodiments of the present system, there is provided a computer readable non-transitory medium having computer readable program code for operating on a computer for performing a method of monitoring capnography signals, the method may include acts of: detecting a concentration of a selected gas in a sample gas flow obtained from a physical interface (107) to a patient (101); forming a dataset including a plurality of data points, each data point corresponding to the detected concentration of the selected gas within the sample gas flow during a sampling time; grouping the data points according to a frequency of occurrence of the data points within the sampling time; and/or determining at least one of a signal confidence and signal quality based on relative characteristics between the groups of data points. It is further envisioned that the act of grouping the data points may include an act of grouping the data points based on different ranges of concentrations of the selected gas. It is further envisioned that the act of determining the at least one of a signal confidence and signal quality may include an act of determining a relative number of data points that are present within the groups of data points. Moreover, it is envisioned that the method may include an act of identifying two groups of data points that may correspondingly have a largest and next largest number of data points amongst the groups of data points. It is further envisioned that the method may include an act of determining a number of data points between the two groups of data points, wherein the act of determining the at least one of a signal confidence and signal quality is based upon the determined number of data points.

The present invention is explained in further detail in the following exemplary embodiments and with reference to the figures, where identical or similar elements may be partly indicated by the same or similar reference numerals, and the features of various exemplary embodiments being combinable. In the drawings:

FIG. 3 shows a graph illustrating a capnogram showing $CO_2$ concentration in a sample gas flow over time in accordance with embodiments of the present system;

FIG. 4A shows a histogram of $CO_2$ signal samples generated in accordance with embodiments of the present system;

FIG. 4B shows a further histogram of $CO_2$ signal samples generated in accordance with embodiments of the present system;

The following are descriptions of illustrative embodiments that when taken in conjunction with the following drawings will demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well known devices, circuits, tools, techniques, and methods are omitted so as not to obscure the description of the present system. It should be expressly understood that the drawings are included for illustrative purposes and do not represent the entire scope of the present system. In the accompanying drawings, like reference numbers in different drawings may designate similar elements.

In accordance with embodiments of the present system, capnograph information may be obtained by the system. The capnograph information may be obtained by any suitable capnography system such as side-stream capnography system. However, it is also envisioned that embodiments of the present system may be operative with other types of capnography systems such as main-stream capnography systems and the like. However, for the sake of clarity, operation with a side-stream capnography system is described herein.

Figure 1:
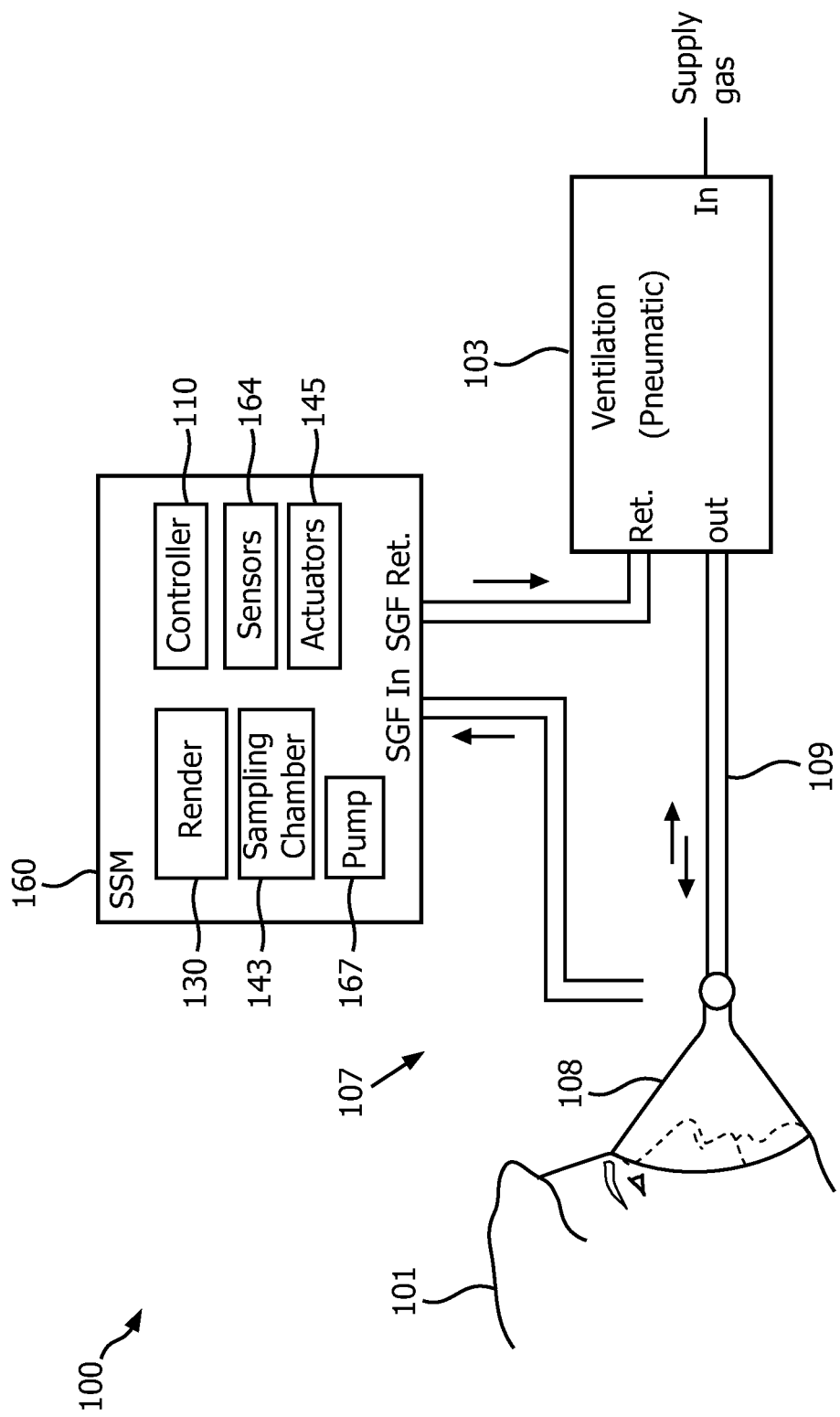
FIG. 1 shows a block diagram of a portion of system in accordance with embodiments of the present system.

For example, FIG. 1 shows a block diagram of a side-stream capnometry system 100 (hereinafter system 100 for the sake of clarity) operating in accordance with embodiments of the present system. The system 100 may include a side-steam monitor (SSM) 160 which may be coupled to a ventilation portion 103 using any suitable method so as to receive a sample gas flow (SGF) at an input (SGF IN). In accordance with embodiments of the present system, the SSM 160 may analyze at least a portion (e.g., a sample portion) of the SGF using one or more sensors 164, and output the SGF at an output (SGF RET). The output SGF may then be provided to a desired portion such as the ventilation portion 103 or vented to atmosphere, if desired. Although a side-steam capnometry system 100 is shown, in accordance with yet other embodiments, it is envisioned that a main-stream capnometry system may provide capnograph information to the system.

The ventilation portion 103 (e.g., a pneumatic portion) may provide a gas for ventilation (hereinafter ventilation gas) of a patient 101. Accordingly, the ventilation portion may receive one or more gasses (e.g., $O_2$, nitrogen ($N_2$), air, water vapor, etc.) at an input end (IN), mix these gasses to form the ventilation gas, and output the ventilation gas at an output (OUT). Accordingly, the ventilation gas may, depending upon system settings and/or time, include a single gas (e.g., $O_2$) or a gas mixture such as an $N_2$ and $O_2$ gas mixture, etc. The ventilation portion 103 may be coupled to a patient 101 using any suitable coupling such as a ventilation coupler 107 which may include one or more hoses 109 and/or a patient interface 108. While the hose typically is not bi-directional (i.e., fluid such as oxygen flows towards the patient 101) in accordance with embodiments of the present system, the hose might occasionally be bi-directional.

In accordance with embodiments of the present system, the system is provided during spontaneous ventilation, when no ventilator is connected to the patient, since that is a time when breath detection is most unreliable. With a ventilator, it is usually known when a breath is delivered. As such in accordance with embodiments of the present system, the ventilation portion may simply be a hose that is coupled to a supply of supplemental oxygen. It is also possible to use this invention without any ventilation portion or when the ventilation portion is otherwise disabled and the patient is merely breathing ambient air (e.g., air that is not enhanced with the introduction of additional or primary gases).

The patient interface 108 may be any suitable type of system interface such as an invasive (an intubation tube, etc.) and/or non-invasive (e.g., a mask as shown, a nasal adapter, a nasal cannula, etc.) type to provide the ventilation gas to the patient 101 for inspiration. The patient interface 108 may include a holding portion such as tabs, straps, etc., which may hold the patient interface 108 in position relative to the patient 101 during use, as desired. In use, the ventilation coupler 107 may further receive exhaled gasses (e.g., expiration gasses) from the patient 101 such as gasses within the respiratory tract of the patient. Accordingly, the SGF may, at certain times, include at least some of these exhaled gasses as described herein. The ventilation portion 103 may include one or more pumps to pressurize an input gas such as air, and/or to provide a desired flow rate, pressure, etc. of the ventilation gas.

In accordance with embodiments of the present system, the ventilation coupler 107 may include one or more passive or active valves such as passive one-way valves which may direct the flow of gasses within the ventilation coupler in a desired direction or directions. For example, the ventilation gas may be provided to the patient 101 for inspiration and expiration gases from the patient 101 may be directed in a different direction. In accordance with embodiments of the present system, the ventilation coupler 107 may further include conditioners such as dryers which may, for example, remove moisture from the SGF and/or trap condensation, as desired. Further, in accordance with embodiments of the present system, the ventilation portion 103 may include pumps, valves, and/or mixers operating under the control of the controller 110 to mix water vapor, and/or medication into the ventilation gas, as desired. The ventilation portion 103 may include a return port to receive a return gas for further processing, if desired. Thereafter, this return gas, or portions thereof, may be mixed with the ventilation gas to be output to the ventilation coupler 107 for reuse, if desired.

Referring back to the SSM 160, in accordance with embodiments of the present system, this portion may include one or more of sensors 164, the controller 110, actuators 165, a pump 167, a sampling chamber 143, and a rendering portion 130. In accordance with embodiments of the present system, the controller 110 may control one or more portions of the overall operation of the SSM 160. For example, the actuators 165 may include one or more motors, transducers, etc. which may provide a force to operate one or more valves, mixers, or the like of the SSM 160 under the control of the controller 110. The sampling chamber 143 may include one or more sampling chambers in which a sample portion of the SGF may be analyzed by the sensors 164. The pump 167 may be operative under the control of the controller 110 to control a flow of the SGF as described.

The sensors 164 may include at least one sensor which may analyze at least a portion of the SGF within the sampling chamber 143. Further, the sensors 164 may include temperature, volume, concentration, and/or pressure sensors to detect temperature, volume, concentration, and/or pressure, respectively, of the SGF within the sampling chamber 143 in accordance with embodiments of the present system. In accordance with embodiments of the present system, the sensors 164 may include electrooptic sensors which may analyze the SGF and determine characteristics of one or more gasses within the SGF such as the presence, temperature, concentration, volume and/or pressure of one or more gasses within the SGF which may be located within the sampling chamber 143. The sensors 164 may then form corresponding sensor information and provide this information to the controller 110 for further processing.

In accordance with embodiments of the present system, the controller 110 may then render the results of the analysis using any suitable rendering device 130 such as a display. The rendering device may be locally and/or remotely located and may communicate with the controller 110 via any suitable bus or network such as the Internet, etc. In accordance with embodiments of the present system, the sensors 164 may be tuned or otherwise configured to detect presence and/or characteristic of a desired gas (e.g., $CO_2$, $O_2$, $N_2$, etc.). Accordingly, the sensors 164, may detect one or more corresponding gasses within the SGF such as carbon dioxide ($CO_2$), oxygen ($O_2$), nitrogen ($N_2$), etc., and may form corresponding sensor information. For purposes of simplifying the description of embodiments of the present system, the system will be described with regard to detection of only characteristics of carbon dioxide ($CO_2$) in the SGF by the sensors 164. However, as may be readily appreciated, characteristics of other gases and/or combinations thereof in the SGF may be sensed by the sensors 164 in accordance with embodiments of the present system.

The controller 110 may then analyze the sensor information to determine characteristics of the sensed gas over time. Once characteristics of the one or more sensed gas are determined such as concentration, the controller 110 may then control the renderer 130 to render results of the determination.

Referring back to the ventilation portion 103, in accordance with embodiments of the present system, this portion may be controlled by a ventilation controller, the controller 110 and/or other controller so as to provide the ventilation gas for ventilating the patient 101 at a desired volume, flow, pressure, and/or mixture.

Figure 2:
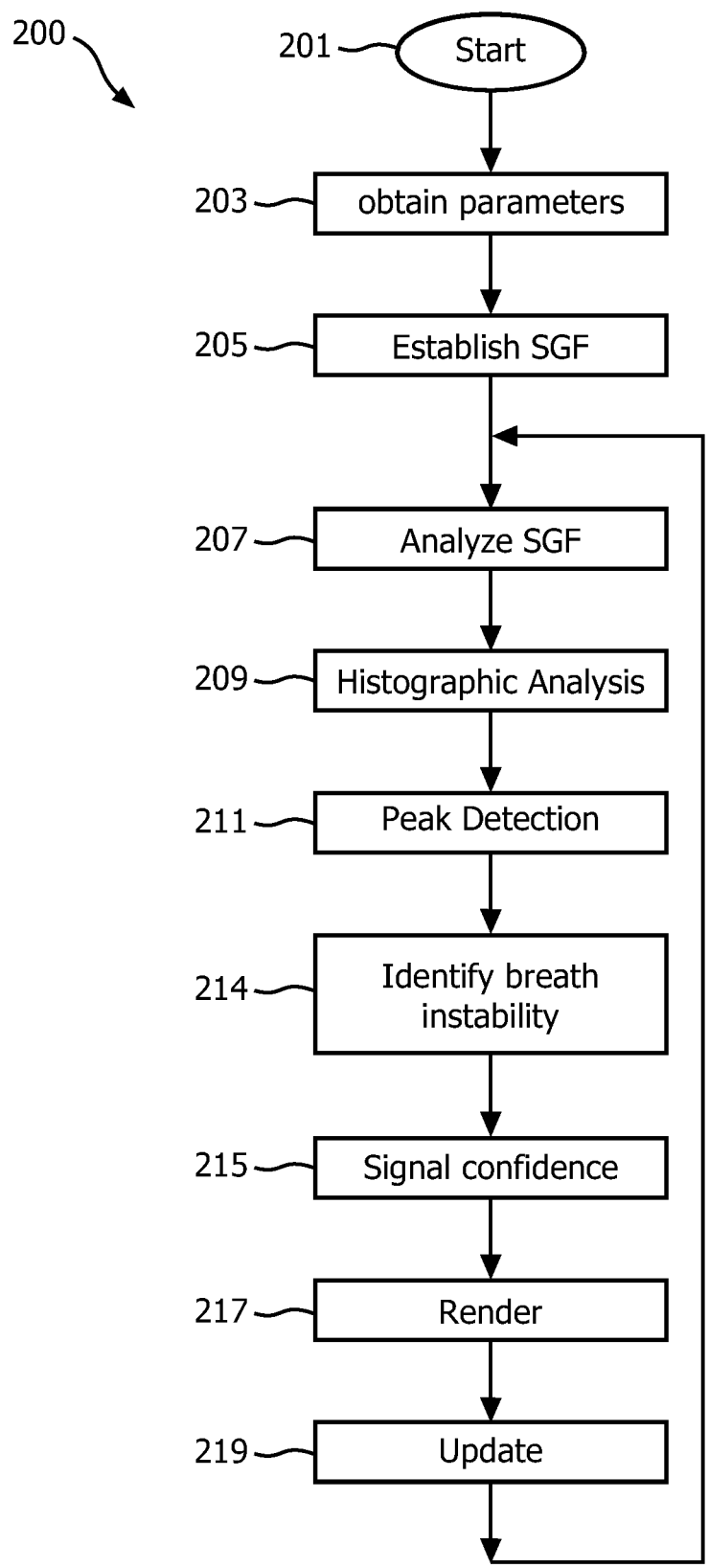
FIG. 2 shows a functional flow diagram performed by a process in accordance with embodiments of the present system.

FIG. 2 shows a functional flow diagram performed by a process 200 in accordance with embodiments of the present system. The process 200 may be performed using one or more processors, computers, controllers, etc., communicating over a network and may obtain information from, and/or store information to one or more memories which may be local and/or remote from each other. The process 200 may include one of more of the following acts. In accordance with embodiments of the present system, the acts of process 200 may be performed using one or more suitable gas monitoring system(s) such as a side-stream monitoring system (SSM) operating in accordance with embodiments of the present system. Further, one or more of these acts may be combined, reordered, and/or separated into sub-acts, as desired. Further, one or more of these acts may be skipped depending upon settings. In operation, the process may start during act 201 and then proceed to act 203.

During act 203, the process may obtain initial operating parameters such as one or more sampling values, a sample flow rate (SFR) value, information about a ventilated patient (e.g., the patient to be ventilated), etc. In accordance with embodiments of the present system, the initial sampling value may denote a sampling time period (e.g., 120 sec.). In accordance with embodiments of the present system, a larger sampling volume may be accommodated by utilizing additional sensors and/or sensors provided with a larger sampling capacity without extending the sampling period. In either event, the sampling volume and/or other characteristic may be set by the system, a user and/or may be obtained from a memory of the system. The sampling time may be set such that capnometry information for a sufficient sampling time may be acquired for analysis.

The capnometry information may include one or more capnographic signals such as a $CO_2$ signal. The sampling value may be set by the system and/or user and may be obtained from a memory of the system. In accordance with embodiments of the present system, the sampling value may be adjusted by the system in real time during operation of the current process, as desired. However, the sampling value should be set so that a data for a sufficient number of breaths (e.g., of a patient) may be collected and analyzed in accordance with embodiments of the present system. Further, the process may obtain a sample flow rate (SFR) value which may be used to initialize a sample gas flow pump of the system. The SFR value may be set by the system and/or user and may be obtained from a memory or in real time, as desired. In accordance with embodiments of the present system, the process may adjust the parameters during operation as may be desired. After completing act 203, the process may continue to act 205.

During act 205, the process may establish a sample gas flow (SGF) of the system. Accordingly, the process may control an SGF pump to provide the SGF at a desired sample flow rate as may be set by the SFR value. The SGF may be obtained from one or more SGF tubes coupled to a sampling system interface such as a nasal cannula coupled to the patient and which receives a ventilation gas from the ventilation portion. Before completing this act, the process may wait for a sample period of time to elapse (e.g., 20 sec., etc), so that at least a portion of the SGF may be provided to one or more sampling chambers of the system. For the sake of clarity, it will be assumed that the SGF is obtained from a patient interface (e.g., a physical interface) of the system. The process may further obtain sensor information to determine, for example, an ambient pressure within one or more of the sampling chambers. The process may further determine a sample flow rate of the SGF in real time. Further, the process may control the SGF pump to maintain a fixed sample flow of the SGF in real time based upon the feedback information such as flow rate information obtained from one or more flow rate sensors of the system. After completing act 205, the process may continue to act 207.

During act 207, the process may analyze at least a portion of the SGF and form corresponding capnometry information which may, for example, include information related to the concentration of one or more gasses within the SGF over time such as $CO_2$. More particularly, the capnometry information may include a capnogram signal (for a corresponding gas) which may for example be represented as a plurality of discrete data points (DPs) over time. Thus, each data point may represent a concentration of $CO_2$ at a corresponding time. These data points may be represented graphically as a capnogram signal or capnogram waveform (e.g., $CO_2$) in a rendered capnogram.

FIG. 3 shows a graph 300 illustrating a capnogram showing $CO_2$ concentration in a sample gas flow over time in accordance with embodiments of the present system. The DPs may be represented as a capnogram signal 302 (which may also be referred to as a capnogram waveform) in time. Roughly approximated expiratory (Ep) and inspiratory (Ip) phases are labeled for illustration. A plurality of these data points for a corresponding gas (e.g., $CO_2$) may be grouped to form a data sample for the sampling time ($t_s$) which may correspond to the sampling period.

The process may employ any suitable method or methods to analyze the SGF to form the capnometry information such as may be employed by capnography systems and the like. Although it is envisioned that embodiments of the present system may detect concentration of gasses such as $CO_2$, $O_2$, $N_2$, etc., only concentration $CO_2$ is discussed herein for the sake of clarity. However, in accordance with embodiments of the present system, operations performed by the process with respect to $CO_2$ may be similarly performed with respect to the other gasses, as desired. After completing act 207, the process may continue to act 209.

During act 209, the process may perform a heuristic analysis in which the process may analyze the capnometry information obtained during the sampling time (ts) as a group to, for example, determine, relative frequency of occurrence of each DP of the DPs within the capnometry information during the period of time (e.g., the past 120 seconds) and may form corresponding histogram information using any suitable method. Thus, the process may analyze individual DPs of the capnometry information over the sampling period as a group (e.g., without reference to breathing cycles) and may determine a relative frequency of occurrence of each DP within the sampling time. In accordance with embodiments of the present system, the sampling time may be set such that it covers at least a plurality of breathing cycles (e.g., between 4-20 breathing cycles, etc. where each breathing cycle includes inspiratory and expiratory phases). Accordingly, during this act the process may form a dataset comprising a plurality of data points, with each data point corresponding to a detected concentration of a selected gas (e.g., $CO_2$ in the current example) within the SGF during the sampling time.

In accordance with embodiments of the present system, the process may place the DPs within the sampling time (e.g., the dataset of all DPs) within groups (e.g., bins, groupings, etc.) according to a frequency of occurrence (e.g., by concentration) within the groups (e.g., the bins). This process is illustrated with reference to FIGS. 4A, 4B which show histograms 400A, 400B of $CO_2$ signal samples generated in accordance with embodiments of the present system. These $CO_2$ signal samples may be represented as DPs obtained during the sampling time and may correspond with the DPs of capnometry information such as shown in FIG. 3. In FIG. 4B a histogram 400B is shown of $CO_2$ signal samples generated in accordance with embodiments of the present system. The histogram 400B includes a plurality of bins 402 each of which has a width (W) which may represent a range of $CO_2$ for the corresponding DPs and may include a height which may correspond with a frequency of occurrence of corresponding DPs within the sampling period. In accordance with embodiments of the present system, the height of each bin 402 may represent a total number of DPs within the respective bin.

With regard to the sampling time, in accordance with embodiments of the present system, the process may determine whether capnometry information is available for a period of time equal to the sampling value so that a full data set of DPs may be acquired. Accordingly, in a case wherein it is determined that capnometry information is available for a period of time equal to the sampling value (e.g., an elapsed time is equal to or greater than the sampling value), the process may perform heuristic analysis. However, in a case wherein it is determined that capnometry information is not available for a period of time equal to the sampling value (e.g., the elapsed time is less than the sampling time), the process may continue to collect capnometry information so that a full data set of DPs may be acquired. In this way, it may be ensured that a satisfactory amount of DPs are available to provide heuristic accuracy.

In accordance with embodiments of the present system, the process may analyze the capnometry information available from a start of monitoring and/or may use a running time interval (e.g., the latest 20 seconds, etc.) each of which may define a sampling time (e.g., a sampling period) depending upon settings. However, in accordance with embodiments of the present system, the process may analyze capnometry information from a desired start time to a stop time and/or a desired interval of time which may define the sampling time. For example, in accordance with embodiments of the present system, the process may analyze capnometry information that represents a most recent time interval (e.g., the latest 120 seconds). Thus, referring to FIG. 3, assuming the start time may be represented as the current time (tc) and the sampling time may be denoted by a (ts)=120 seconds in the current example. This sampling period may be represented as tc−ts=tc−120 seconds. It is further envisioned that the process may form a graphical user interface (GUI) with which a user may interact to set these times (e.g., ts, tc, etc.) as desired. For example, with reference to FIG. 3, the process may provide a user with sliders 307 and 309 which the user may slide to select tc and ts, respectively. These times may be set/reset by a user in real time and/or may be stored in a memory of the system for later use. However, in accordance with embodiments or the present system, the sampling time may be predefined and may be stored in a memory of the system and may be obtained by the process during initialization. After completing act 209, the process may then continue to act 211.

During act 211, the process may perform peak detection to estimate an end-tidal (Et) $CO_2$ value for the sampling time. This value may represent an average value of the end tidal (Et) $CO_2$ for the sampling time which, in the current example, includes a plurality of breathing cycles during the sampling time. Peak detection may be performed in accordance with embodiments using a suitable method including for example detection of peaks 401 and 403 of a graph and/or detection of peaks through bin analysis.

For example, with reference to FIG. 4B, a peak detection method performed in accordance with embodiments of the present system may select the bins with the greatest number of DPs (e.g., the highest or largest bins). Thus, assuming that each bin has a corresponding group of DPs, the process may select the largest group of DPs. In accordance with embodiments of the present system, the values of DPs in this selected group may then be averaged and an end-tidal $CO_2$ concentration value may then be set to the results of the averaging.

Thus, in accordance with embodiments of the present system, the process may use a peak detection method to determine an end-tidal $CO_2$ concentration without identifying individual breath cycles. In accordance with embodiments of the present system, this may reduce system resources and erroneous data which may otherwise result when using conventional methods which may for example misidentify individual breath cycles.

Thus, embodiments of the present system may employ a peak-detection method to determine an estimated end-tidal $CO_2$ concentration value without a need to detect individual breath cycles and/or phases (e.g., inspiratory and/or expiratory phases). Rather, the process in accordance with embodiments of the present system, may determine the estimated end-tidal $CO_2$ concentration value based upon an average of end-tidal $CO_2$ concentration values from a plurality of breath cycles during the sampling time and which therefore, need not be individually detected.

In accordance with embodiments of the present system, a method to determine estimated average end tidal $CO_2$ level and estimated value of the inspiratory $CO_2$ for a sampling time is described with reference to FIGS. 3, 4A and 4B. For example, with reference to FIG. 4B, histogram 400B shows bins 402 which have heights that correspond to the number of DPs (or the corresponding $CO_2$ signal) grouped within the corresponding bin 402 for the corresponding sampling time (ts). With reference to FIG. 3, during a breathing cycle (e.g., encompassing inspiratory and expiratory phases), the majority of a time-based capnogram is comprised of the inspiratory phase (Ip) during which the $CO_2$ signal is near-zero and a plateau phase (PP) during which the $CO_2$ signal is relatively stable near the maximum (end-tidal (ET)) $CO_2$ level. The transition periods between the plateau and inspiratory phases are normally quite brief relative to the other two phases (e.g., the inspiratory and expiratory phases).

Referring to FIGS. 4A and 4B, during normal stable breathing, a histogram of the $CO_2$ signal taken over a fixed time interval (e.g., the sampling time) has characteristic peaks indicating a large number of values (e.g., high frequency of occurrences) at each the low (inspiratory phase (Ip)) and the high (plateau phase (PP)) extremes (e.g., of the expiratory phase (Ep)) of the observed $CO_2$ signal values. In accordance with embodiments of the present system, the process may analyze the generated histogram to determine the relative frequency of $CO_2$ signal values (e.g. DPs) that land outside of these two peaks (e.g., the two largest bins of the bins 402 shown in FIG. 4B or the peaks 401 and 403 shown in FIG. 4A) of the histogram. Further, the histogram may be used to identify unstable breathing without a need to detect individual breaths or time-based characteristic features of those breaths.

To perform peak selection, the process may for example analyze the histogram 400A and select the two highest peaks (401 and 403 of all the peaks) or analyze the histogram 400B and select bins 402 with the two largest number of DPs assigned thereto within the histogram from all the bins 402. Of these two largest peaks (401 and 403) or bins 402, the process may determine which peaks/bin corresponds with a larger capnogram signal value (e.g., based upon an average of DPs for example within the corresponding bin 402) and set this peak or bin as a plateau phase (PP) peak (PP_Peak) and may set the other bin(s) 402 as the inspiratory peak (IP_Peak). In accordance with embodiments of the present system, the process may determine an average of the capnogram signal at the plateau-phase peak (PP_Peak) (e.g., by averaging all the DPs within this peak or bin) and set this value as the estimated value of the end tidal (Et) $CO_2$ for the sampling time. Similarly, the process may determine an average of the capnogram signal at the inspiratory peak (IP_Peak) (e.g., by averaging all the DPs within this bin) and set this value as the estimated value of the inspiratory $CO_2$ for the sampling time. After completing act 211, the process may continue to act 214.

During act 214, the process may identify periods of breath instability without a need to identify individual breaths. In accordance with embodiments of the present system, breath instability may be identified in a histogram by observing for example a high number of samples in the middle concentration range, for example between 15 and 25 mmHg. As recognized in accordance with embodiments of the present system, during breath instability, the capnogram does not quickly alternate between low and high concentration points, but remains in the middle range for prolonged periods.

For an ideal capnogram, the majority (>85%) of DPs are located in the two peaks (IP_peak and PP_peak). In accordance with embodiments of the present system, presence of data between these peaks is indicative of unstable breathing. When the size (tidal volume) and rate of breaths changes, then the height of the individual plateaus combine in the histogram to create a lower PP_peak and possibly smaller peaks that are between the IP_peak and the PP_peak. Another source of DPs that are not part of the peaks is capnometry waveforms that do not contain a plateau. In this case, the PP_peak is low or nonexistent with a number of DPs between the IP_peak and the maximum CO2 value found in the histogram. Another indication of unstable breathing is seen when the maximum $CO_2$ value observed in the histogram is much less than the location of the PP_peak. In the ideal histogram, there is little difference between the location of the PP_peak and the maximum $CO_2$ value as indicated by the highest $CO_2$ value for which a DP is found in the histogram. A high difference between the PP_peak location and the max DP location is an indication of unstable breathing. After completing act 214, the process may continue to act 215.

During act 215, the process may determine signal confidence and/or signal quality during the sampling time. In accordance with embodiments of the present system, signal quality may be scored for example using a weighted sum of descriptive parameters calculated from the histogram. For example the average, or peak, of the PP_peak relative to the sampling time may be one parameter. The difference between the PP_peak location and the maximum $CO_2$ may be a descriptive parameter. A smaller difference is indicative of a better quality signal. The sum of DPs that are not part of either the IP_peak or the PP_peak relative to the sampling time may be another parameter. Ideally, the fraction of the DPs that are in neither of the peaks should be low (e.g., less than 20%). A signal quality score may be calculated for example by normalizing each of these parameters by subtracting an offset value and then scaling the parameters up or down by a multiplicative factor. The act of normalizing the inputs may be utilized for example when some parameters are fractions and others are difference values or counts of DPs etc.

In accordance with embodiments of the present system, the signal confidence parameter may be calculated by multiplying each of the normalized descriptive parameters by a weighting factor and summing the results. The weighting factors may be selected for example based on the relative strength of the relationship between the parameter value and signal quality. The signal confidence and/or signal quality may represent a measure of how stable the respiration rate, breath volume (tidal volume) and end-tidal $CO_2$ values are for the sampling time.

Various methods in accordance with embodiments of the present system to determine signal confidence and/or quality for a sampling time are illustratively described with reference to FIGS. 7 through 11 below.

Figure 7A:
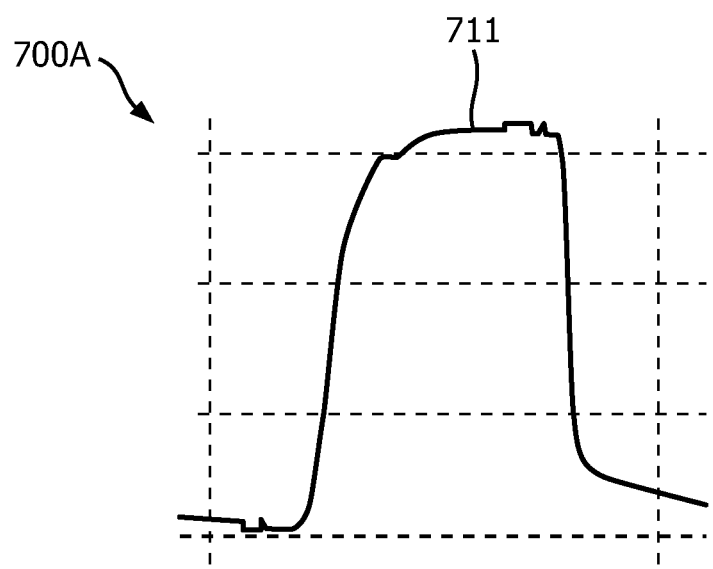
FIG. 7A shows a portion of a capnogram including a $CO_2$ waveform formed in accordance with embodiments of the present system.
Figure 7B:
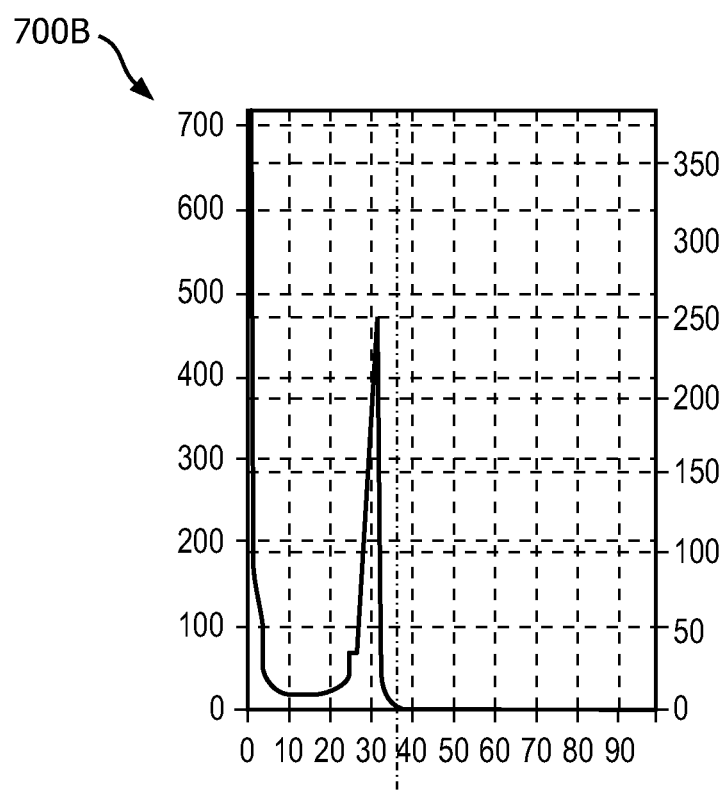
FIG. 7B shows a portion of a histogram corresponding to a capnogram formed in accordance with embodiments of the present system.
Figure 8A:
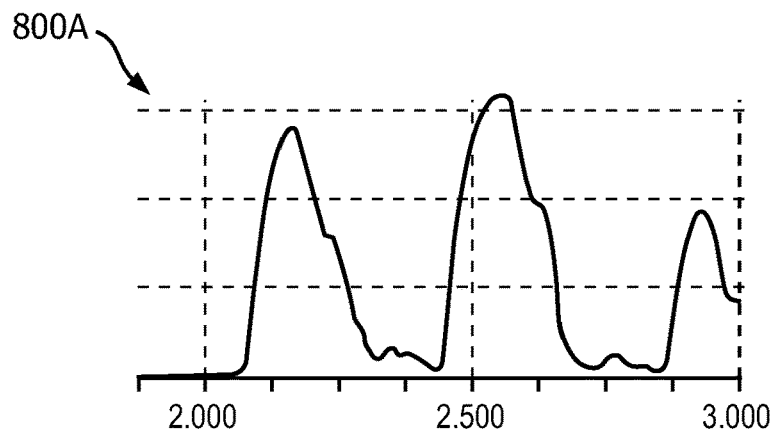
FIG. 8A shows a portion of a capnogram including a $CO_2$ waveform formed in accordance with embodiments of the present system.
Figure 8B:
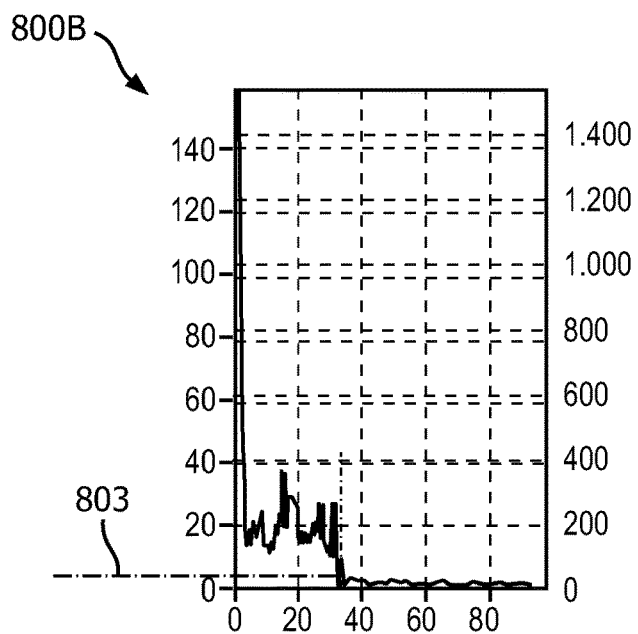
FIG. 8B shows a portion of a histogram corresponding to a capnogram formed in accordance with embodiments of the present system.
Figure 8C:
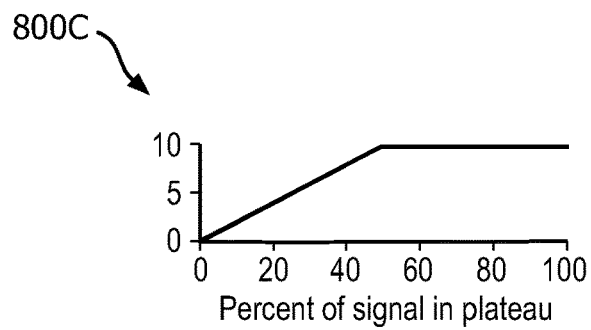
FIG. 8C shows a graph of a feature mapping function generated in accordance with embodiments of the present system.
Figure 9:
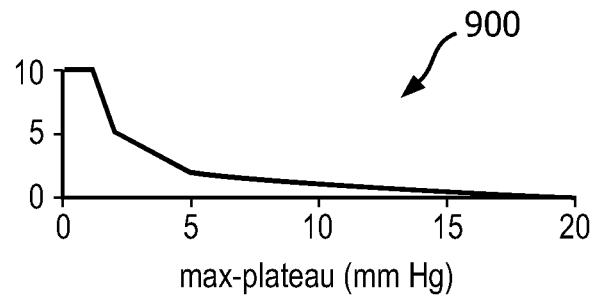
FIG. 9 shows a graph of a feature mapping function generated in accordance with embodiments of the present system.

For example, a method to identify when $CO_2$ waveforms do not include a consistent expiratory plateau is shown and described with reference to FIGS. 7A through 8A. This method may be referred to as a percent plateau method and may determine a $CO_2$ parameter quality index (PQI). More particularly, FIG. 7A shows a portion of a capnogram 700A including a normal $CO_2$ waveform formed in accordance with embodiments of the present system. For the sake of clarity, a normal capnogram may be considered to include a capnographic signal with a consistent expiratory plateau 711 for example as shown. FIG. 7B shows a portion of a histogram 700B corresponding to the capnogram 700A formed in accordance with embodiments of the present system. FIG. 8A shows a portion of a capnogram 800A including a $CO_2$ waveform without a consistent expiratory plateau formed in accordance with embodiments of the present system. FIG. 8B shows a portion of a histogram 800B corresponding to the capnogram 800A formed in accordance with embodiments of the present system. The method may include an algorithm which may analyze histograms formed in accordance with embodiments of the present system. The algorithm may identify within the histogram baseline samples for example treating everything less than a threshold value, for example of ($maxCO_2$−$minCO_2$)/2 as baseline data. For example, the algorithm in accordance with embodiments may identify all data within a range (e.g., peak location −5 mm Hg and the peak location +2 mm Hg) and set this data as plateau data. The percent plateau may then be calculated for example as 20 times the plateau sample count divided by the non-baseline sample count. In accordance with embodiments of the present system, the algorithm may update frequency for example every five seconds (however other update frequencies are also envisioned in accordance with embodiments of the present system). With reference to FIG. 8C, a feature mapping function is shown and may illustrate a percent of a signal within the plateau. In accordance with embodiments of the present system, an illustrative $CO_2$ PQI Weighting factor may be set for example equal to 0.25 although other weighting factors may be similarly applied.

It is further envisioned that embodiments of the present system may include a method to identify when there may be breath-to-breath differences in a $CO_2$ waveform of a capnographic signal. This method is illustratively described with reference to FIG. 9 which shows a graph 900 of a feature mapping function generated in accordance with embodiments of the present system. The method may include an algorithm which may determine a difference between a plateau $CO_2$ (e.g., a plateau value) as calculated from a histogram and a max observed $CO_2$ during a period such as for example the past 30 seconds. The plateau value may be determined as a most commonly occurring $CO_2$ value that is higher than the midpoint between the max and min $CO_2$ during the prior 30 seconds. The update frequency for this algorithm may be set to any desired value such as 5 seconds. Further, this algorithm may employ a weighing factor (e.g., a $CO_2$ PQI Weighting factor=0.25).

It should be noted that while the above illustrates algorithms for example in accordance with embodiments of the present system, other calculations (e.g., different plateau value calculations, weighting factors, etc.) are also considered in accordance with embodiments of the present system. For example, when unstable breathing is determined, the algorithm may render a message such as "Unstable Breathing." Accordingly, this parameter may be used to identify breath-to-breath differences in the CO2 waveform such as a case wherein there may be for example a single elevated $CO_2$ value and the rest of the waveform plateaus are lower. In accordance with embodiments, the algorithm may consider the $CO_2$ signal during a period such as the previous 30 seconds, there may be a chance that a most commonly occurring plateau and the maximum $CO_2$ during the 30 second window are very different. In a stable capnogram, the difference should be small, such as less than 4 mm Hg. When there is a large difference between the plateau and the max (e.g., the max occurring $CO_2$), this is an indication of unstable breathing. For example, a difference of 7 mm Hg or more may be utilized to indicate unstable breathing. In accordance with embodiments, a larger indication may be utilized to indicate very unstable breathing. For example, in accordance with embodiments, a difference greater than 10 mm Hg may be utilized to indicate that the breathing is very unstable.

Figure 10:
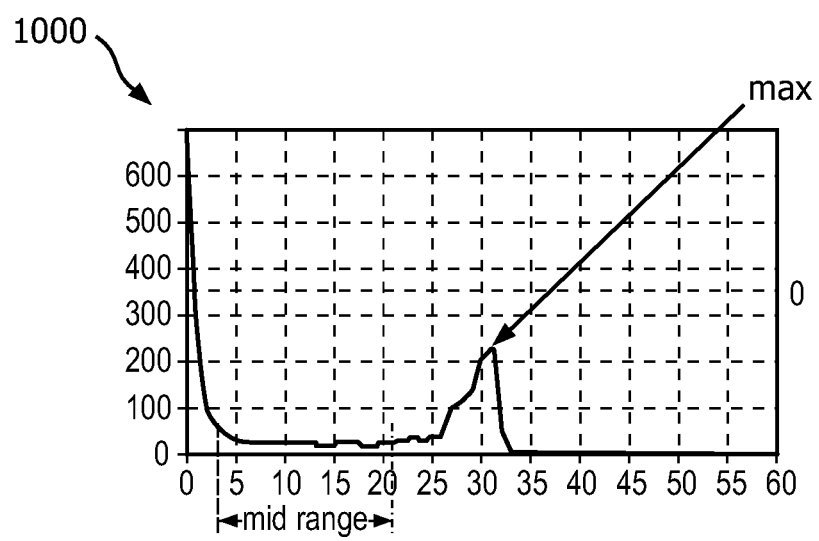
FIG. 10 shows a portion of a histogram corresponding to a capnogram formed in accordance with embodiments of the present system.
Figure 11:
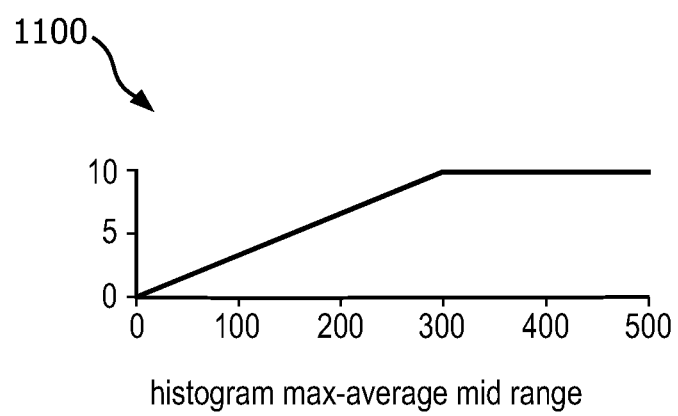
FIG. 11 shows a graph of a feature mapping function generated in accordance with embodiments of the present system.

A method to identify when a capnogram lacks a common plateau value during an analysis period will now be described with reference to FIGS. 10 and 11. FIG. 10 shows a portion of a histogram 1000 corresponding to a capnogram formed in accordance with embodiments of the present system. FIG. 11 shows a graph 1100 of a feature mapping function generated in accordance with embodiments of the present system. Generally, when a capnogram spends a disproportionate time in the transition and not at either the plateau or trough, a value formed in accordance with embodiments of the present system may be low. The method may include an algorithm which may analyze a histogram such as the histogram shown in FIG. 10 to find a most commonly occurring high value (max) that may be used to represent a plateau of a plateau phase. Then, the algorithm may calculate an average histogram value in a range between a low peak (trough) +z and a location of a maximally occurring high peak −z, where z=5. Then, the algorithm may determine a difference between the max value and a mid-range value as shown. The algorithm may include an update frequency of, for example, 5 seconds. Accordingly, the histogram may be analyzed every 5 seconds. A feature mapping function of this algorithm may be similar to that shown in FIG. 11. The algorithm may include a weighing factor such as equal to 0.25. When it is determined that there is a low tidal volume, the algorithm may render a message such as "LOW TIDAL VOLUME DETECTED".

In accordance with embodiments of the present system, the process may further compare the signal confidence or quality for the current sampling time with the signal confidence or quality, respectively, for a previous sampling time (e.g., a most recent or other selected sampling time as may be selected by the system and/or user) and determine a signal trend. For example, in a case wherein the signal quality of the current sampling time is determined to have improved, the signal quality trend indicator may be represented as a score such as 10 out of 10, 100 out of 100 (etc.), a "+" and/or a green highlight. Conversely, in a case wherein the signal quality of the current sampling time is determined to have not improved, the signal quality trend indicator may be represented as a score such as 1 out of 10, 1 out of 100 (etc.), a "−" and/or a red highlight. Finally, in a case wherein no change is detected in the signal quality, the signal quality trend indicator may be represented as a "0" as the same score as the previous signal quality indicator, and/or a gray highlight. In accordance with embodiments of the present system, the process may determine signal confidence trend indicators similarly.

Figure 5:
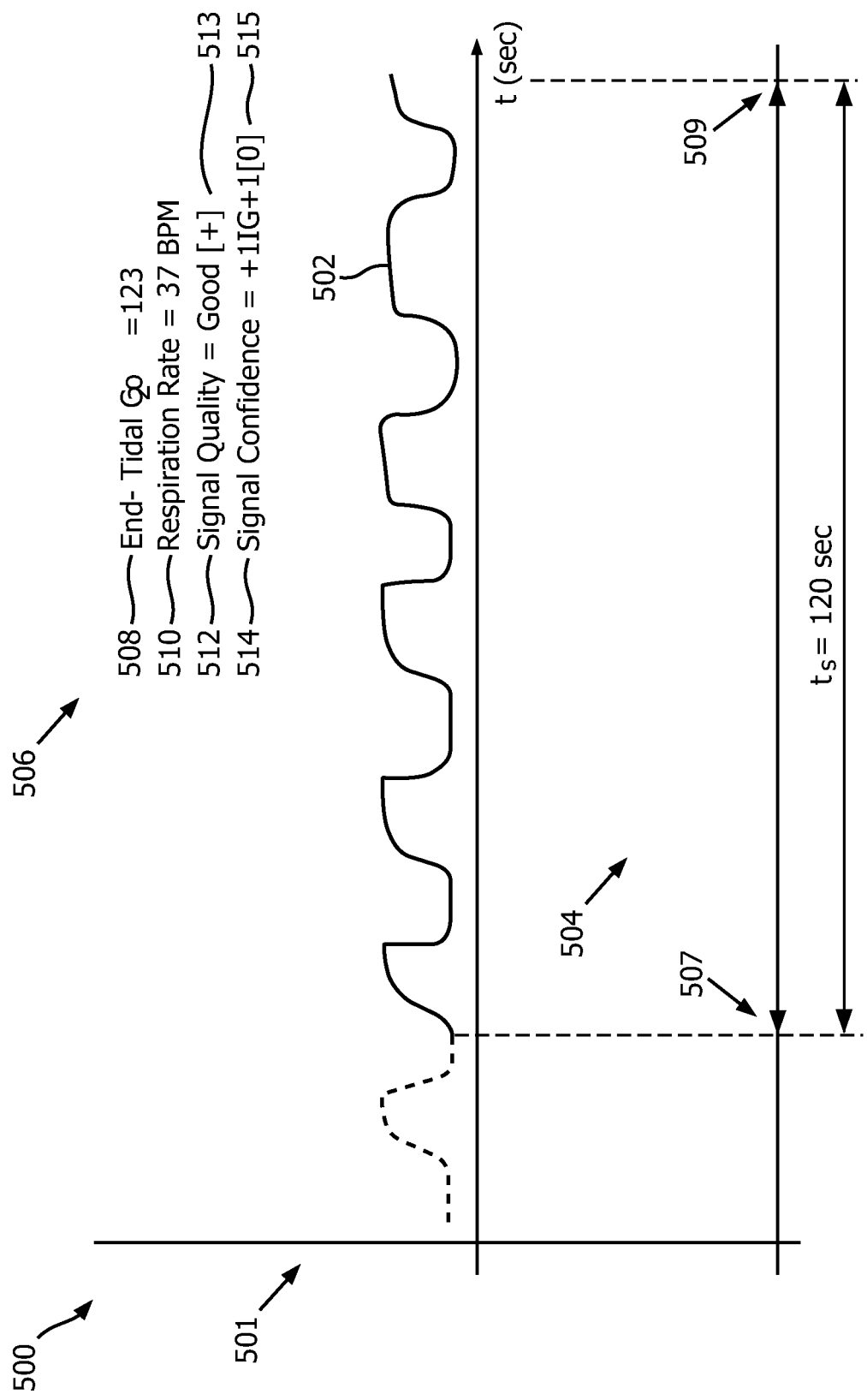
FIG. 5 shows a graph of a screen rendering in accordance with embodiments of the present system.

During act 217, the process may render results of the process. For example, the process may render one or more of the determined capnometry signals, the end-tidal $CO_2$ value, the estimated respiration rate, the signal confidence, the signal quality, the signal confidence trend indicator, and the signal quality trend indicator for the corresponding sampling time. For example, FIG. 5 shows a graph 500 including a capnogram 501 rendered in accordance with embodiments of the present system. More particularly, the graph 500 may include information generated by the process such as one or more of a capnogram 501, a capnometry signal 502, a sampling time selection menu slider 504, for example including include sliders 507 and/or 509, and a menu 506. The sliders 507 and/or 509 may be utilized (e.g., moved) to select tc and ts, respectively. In accordance with embodiments of the present system, to increase the sampling time, the user may drag the slider 507 to the left and set the slider 509 in a right-most position.

The menu 506 may include results of the process such as information related to one or more of an end-tidal $CO_2$ value 508, respiratory rate 510, signal quality 512, and signal confidence 514. Further, as shown the signal quality 512 and signal confidence 514 may include corresponding signal trend indicators 513 and 515, respectively, illustratively shown in brackets. In accordance with embodiments of the present system, the present system may also display a clinical message related to the information contained in the histogram such as a message related to whether or not there are detected periods of slow and/or inadequate breathing. The process may further provide a method for a user to interact with the system, as desired. Accordingly, for example, the process may provide an interactive menu (e.g., user interface, UI) for a user to interact with the system to change parameters, system settings, store information, etc. For example, in accordance with embodiments of the present system, the user may use the sliders 507 and/or 509 to change a sampling time in real time as may be desired. After completing act 217, the process may continue to act 219.

During act 219, the process may update a system history which may be stored in a memory of the system to record results of the process. In accordance with embodiments of the present system, the process may thereafter repeat act 207, etc. as shown. In accordance with embodiments of the present system, the process may end when an end signal is detected. The end signal may be generated for example by a user and/or the system such as when disconnection of the physical interface is detected or otherwise indicated.

Figure 6:
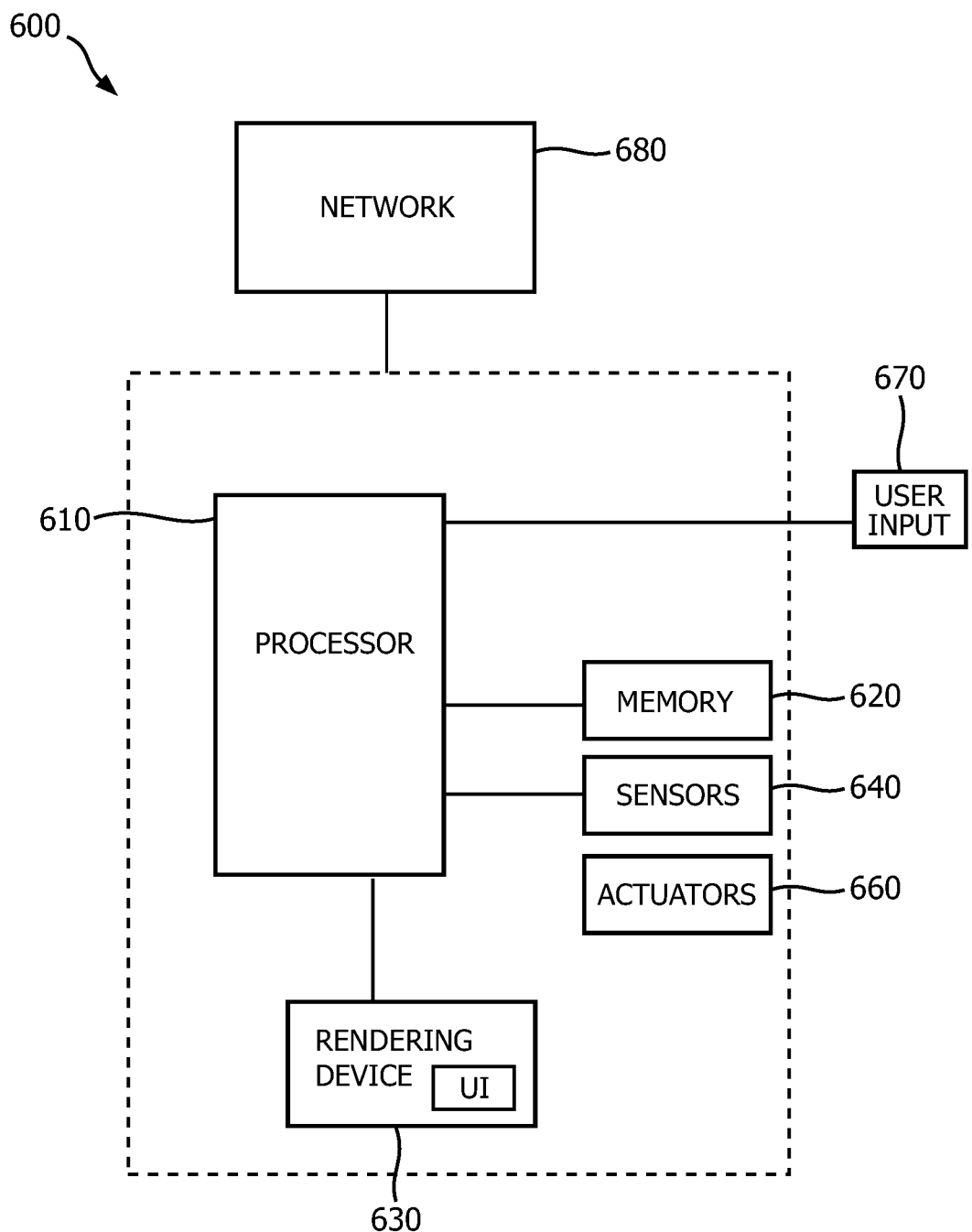
FIG. 6 shows a portion of a system in accordance with embodiments of the present system.

FIG. 6 shows a portion of a system 600 in accordance with embodiments of the present system. For example, a portion of the present system may include a processor 610 (e.g., a controller) operationally coupled to a memory 620, a rendering device such as a display 630, sensors 640, actuators 660, a network 680, and a user input device 670. The memory 620 may be any type of device for storing application data as well as other data related to the described operation. The application data and other data are received by the processor 610 for configuring (e.g., programming) the processor 610 to perform operation acts in accordance with the present system. The processor 610 so configured becomes a special purpose machine particularly suited for performing in accordance with embodiments of the present system.

The user input 670 may include a keyboard, a mouse, a trackball, or other device, such as a touch-sensitive display, which may be stand alone or be a part of a system, such as part of a personal computer, a personal digital assistant (PDA), a mobile phone (e.g., a smart phone), a monitor, a wearable display (e.g., smart glasses, etc.), a smart- or dumb-terminal or other device for communicating with the processor 610 via any operable link. The user input device 670 may be operable for interacting with the processor 610 including enabling interaction within a user interface (UI) as described herein. Clearly the processor 610, the memory 620, display 630, and/or user input device 670 may all or partly be a portion of a computer system or other device such as a client and/or server type device.

The actuators 660 may include one or more motors, transducers, etc. which may provide a force to operate one or more valves, mixers, or the like of the SSM 160 under the control of the processor 610. These valves may, for example, include pneumatic control valves which may control the flow of one or more gasses for ventilation, etc.

The methods of the present system are particularly suited to be carried out by a computer software program, such program may contain one or more modules corresponding to one or more of the individual steps or acts described and/or envisioned by the present system. Such program may of course be embodied in a computer-readable medium, such as an integrated chip, a peripheral device or memory, such as the memory 620 or other memory coupled to the processor 610.

The program and/or program portions contained in the memory 620 may configure the processor 610 to implement the methods, operational acts, and functions disclosed herein. The memories may be distributed, for example between the clients and/or servers, or local, and the processor 610, where additional processors may be provided, may also be distributed or may be singular. The memories may be implemented as electrical, magnetic or optical memory, or any combination of these or other types of storage devices. Moreover, the term "memory" should be construed broadly enough to encompass any information able to be read from or written to an address in an addressable space accessible by the processor 610. The memory 620 may include a non-transitory memory. With this definition, information accessible through a network such as the network 680 is still within the memory, for instance, because the processor 610 may retrieve the information from the network 680 for operation in accordance with the present system.

The processor 610 is operable for providing control signals and/or performing operations in response to input signals from the user input device 670 as well as in response to other devices of a network and executing instructions stored in the memory 620. The processor 610 may include one or more of a microprocessor, an application-specific or general-use integrated circuit(s), a logic device, etc. Further, the processor 610 may be a dedicated processor for performing in accordance with the present system or may be a general-purpose processor wherein only one of many functions operates for performing in accordance with the present system. The processor 610 may operate utilizing a program portion, multiple program segments, or may be a hardware device utilizing a dedicated or multi-purpose integrated circuit.

Accordingly, embodiments, of the present system may provide an enhanced gas monitoring system such as a side-stream $CO_2$ monitoring system for in-patient as well as out-patient procedures and care which may analyze a capnometry signal to determine one or more characteristics of the signal such as signal quality, confidence, breaths-per-minute (BPM), and end-tidal $CO_2$ values. Accordingly, embodiments of the present system may provide a side-stream $CO_2$ monitoring system that may be used with, for example, critical-care ventilators, home ventilators, multi-parameter monitors and the like. Further, it is envisioned that these $CO_2$ monitoring systems operating in accordance with embodiments of the present system may be used in various medical environments such as endoscopy suites, intensive-care units (ICU), operating rooms (OR), emergency rooms, ambulatory care, and/or other medical facilities.

While the present invention has been shown and described with reference to particular exemplary embodiments, it will be understood by those skilled in the art that present invention is not limited thereto, but that various changes in form and details, including the combination of various features and embodiments, may be made therein without departing from the spirit and scope of the invention.

Further variations of the present system would readily occur to a person of ordinary skill in the art and are encompassed by the following claims.

Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function;

e) any of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices or portions thereof may be combined together or separated into further portions unless specifically stated otherwise;

h) no specific sequence of acts or steps is intended to be required unless specifically indicated;

i) the term "plurality of" an element includes two or more of the claimed element, and does not imply any particular range of number of elements; that is, a plurality of elements may be as few as two elements, and may include an immeasurable number of elements; and j) the term and/or and formatives thereof should be understood to mean that only one or more of the listed elements may need to be suitably present in the system in accordance with the claims recitation and in accordance with one or more embodiments of the present system.

The invention claimed is:

1. A gas concentration monitoring system, comprising:
a sensor;
a rendering device;
a processor coupled to the sensor and the rendering device, where the processor is configured to:
receive sensor information from the sensor;
determine a concentration of a selected gas from the sensor information that is received by the processor for a sample gas flow obtained from a physical interface to a patient;
form a dataset comprising data points, each data point of the data points corresponding to the determined concentration of the selected gas within the sample gas flow at a given time during a sampling time interval, wherein the sampling time Interval encompasses a plurality of breaths including inspiratory and expiratory breaths;
group the data points to form groups of data points according to a frequency of occurrence of the data points within the sampling time interval, wherein the groups of data points are formed irrespective of when a given data point of the data points occurs within the sampling time interval;

determine at least one of a signal confidence and signal quality for the sampling time interval based on relative characteristics between the groups of data points; and render on the rendering device the determined at least one of the signal confidence and the signal quality.

2. The gas concentration monitoring system of claim 1, wherein the processor is configured to group the data points with each grouping corresponding to a different range of concentrations of the selected gas irrespective of when the given data point occurs within the sampling time interval.

3. The gas concentration monitoring system of claim 1, wherein the processor is configured to determine the at least one of the signal confidence and the signal quality based upon a relative number of data points that are present within the groups of data points.

4. The gas concentration monitoring system of claim 1, wherein the processor is configured to render the groups of data points as a histogram on the rendering device, and wherein a height of the histogram representation of a given group of the groups of data points indicates a cumulative frequency of occurrence of the data points irrespective of when the given data point occurs within the sampling time interval.

5. The gas concentration monitoring system of claim 1, wherein the processor is configured to identify two groups of data points of the groups of data points that correspondingly have a largest and next largest number of data points amongst the groups of data points.

6. The gas concentration monitoring system of claim 5, wherein the processor is configured to determine a number of data points between the two groups of data points and is configured to determine the at least one of a signal confidence and signal quality based upon the determined number of data points.

7. The gas concentration monitoring system of claim 1, wherein the sampling period of time interval encompasses at least a period of at least 20 seconds.

8. The gas concentration monitoring system of claim 1, comprising the physical interface, wherein the physical interface comprises a nasal cannula or mask configured for coupling to the patient.

9. The gas concentration monitoring system of claim 1, further comprising a pneumatic system controlled by the processor to provide a ventilation gas mixture to the physical interface for inhalation by the patient.

10. A method of monitoring capnography signals comprising acts of:

determining, using a processor, a concentration of a selected gas in a sample gas flow obtained from a physical interface to a patient;

forming, using the processor, a dataset comprising data points, each data point of the data points corresponding to the determined concentration of the selected gas within the sample gas flow at a given time during a sampling time interval;

grouping, using the processor, the data points to form groups of data points according to a frequency of occurrence of the data points within the sampling time Interval, wherein the groups of data points are formed Irrespective of when a given data point of the data points occurs within the sampling time Interval;

determining, using the processor, at least one of a signal confidence and signal quality for the sampling time interval based on relative characteristics between the groups of data points; and rendering, using a rendering device, the determined at least one of the signal confidence and the signal quality.

11. The method of claim 10, wherein the act of grouping the data points comprises an act of grouping the data points based on different ranges of concentrations of the selected gas irrespective of when the given data point occurs within the sampling time interval.

12. The method of claim 10, wherein the act of determining the at least one of the signal confidence and the signal quality comprises an act of determining a relative number of data points that are present within the groups of data points.

13. The method of claim 10, wherein the act of rendering the groups of data points comprises an act of rendering the groups of data points as a histogram on a rendering device, and wherein a height of the histogram representation of a given group of the groups of data points Indicates a cumulative frequency of occurrence of the data points irrespective of when the given data point occurs within the sampling time Interval.

14. The method of claim 10, comprising an act of identifying two groups of data points of the groups of data points that correspondingly have a largest and next largest number of data points amongst the groups of data points.

15. The method of claim 14, comprising an act of determining a number of data points, wherein the act of determining the at least one of a signal confidence and signal quality is based upon the determined number of data points.

16. The method of claim 10, wherein the sampling time interval encompasses a period of at least 20 seconds.

17. A computer readable non-transitory medium having computer readable program code for causing a data processing device to perform a method of monitoring capnography signals, the method comprising acts of:

determining a concentration of a selected gas from sensor information for a sample gas flow obtained from a physical interface to a patient;

forming a dataset comprising data points, each data point corresponding to the determined concentration of the selected gas within the sample gas flow at a given time during a sampling time interval;

grouping the data points to form groups of data points according to a frequency of occurrence of the data points within the sampling time interval, wherein the groups of data points are formed irrespective of when a given data point of the data points occurs within the sampling time interval;

determining at least one of a signal confidence and signal quality for the sampling time based on relative characteristics between the groups of data points; and initiating a rendering on a rendering device of the determined at least one of the signal confidence and the signal quality.

18. The medium of claim 17, wherein the act of grouping the data points comprises an act of grouping the data points based on different ranges of concentrations of the selected gas irrespective of when the given data point occurs within the sampling time interval.

19. The medium of claim 17, wherein the act of determining the at least one of the signal confidence and the signal quality comprises an act of determining a relative number of data points that are present within the groups of data points.

20. The medium of claim 17, the method comprising an act of identifying two groups of data points of the groups of data points that correspondingly have a largest and next largest number of data points amongst the groups of data points, and the method further comprising an act of determining a number of data points between the two groups of data points, wherein the act of determining the at least one of the signal confidence and the signal quality is based upon the determined number of data points.

* * * * *